(12) United States Patent
Viyannalage et al.

(10) Patent No.: US 10,790,482 B2
(45) Date of Patent: Sep. 29, 2020

(54) LITHIUM-IODINE ELECTROCHEMICAL CELLS EXHIBITING LOW DISCHARGE IMPEDANCE

(71) Applicant: Greatbatch Ltd., Clarence, NY (US)

(72) Inventors: Lasantha Viyannalage, Pittsford, NY (US); Adrish Ganguly, Clarence, NY (US); Ashish Shah, East Amherst, NY (US); David Panek, Alden, NY (US)

(73) Assignee: Greatbatch Ltd., Clarence, NY (US)

( * ) Notice: Subject to any disclaimer, the term of this patent is extended or adjusted under 35 U.S.C. 154(b) by 74 days.

(21) Appl. No.: 16/048,984

(22) Filed: Jul. 30, 2018

(65) Prior Publication Data

US 2019/0044101 A1 Feb. 7, 2019

Related U.S. Application Data

(60) Provisional application No. 62/541,512, filed on Aug. 4, 2017.

(51) Int. Cl.
| | |
|---|---|
| *H01M 2/02* | (2006.01) |
| *H01M 4/13* | (2010.01) |
| *H01M 6/18* | (2006.01) |
| *C22C 38/40* | (2006.01) |
| *A61N 1/375* | (2006.01) |

(Continued)

(52) U.S. Cl.
CPC .......... *H01M 2/0287* (2013.01); *A61N 1/362* (2013.01); *A61N 1/378* (2013.01); *A61N 1/37512* (2017.08); *C22C 38/40* (2013.01); *H01M 2/028* (2013.01); *H01M 2/0285* (2013.01); *H01M 2/065* (2013.01); *H01M 4/13* (2013.01); *H01M 4/382* (2013.01); *H01M 4/388* (2013.01); *H01M 4/662* (2013.01); *H01M 6/182* (2013.01);
(Continued)

(58) Field of Classification Search
None
See application file for complete search history.

(56) References Cited

U.S. PATENT DOCUMENTS

| | | |
|---|---|---|
| 3,660,163 A | 5/1972 | Moser |
| 3,674,562 A | 7/1972 | Schneider et al. |
(Continued)

OTHER PUBLICATIONS

Extended European Search Report, Application No. 18187169.0, dated Oct. 1, 2018.
(Continued)

*Primary Examiner* — Daniel S Gatewood
(74) *Attorney, Agent, or Firm* — Michael F. Scalise

(57) ABSTRACT

An lithium-iodine electrochemical cell and method of making is described. The cell comprises a lithium anode and a cathode of a charge transfer complex which includes iodine and preferably polyvinylpyridine. The iodine-containing cathode is in operative contact with both the anode the cell casing serving as the cathode current collector. Preferably the casing is composed of stainless steel that has been thermally annealed at temperatures of 1,800° F. or less. The annealed stainless steel has a grain size of about ASTM 7 or finer. When the iodine-containing cathode material in liquid form is filled into the casing, it contacts the inner casing surface. The passivation layer that subsequently forms at the contact interface affects cell impedance during discharge. It is desirable to maintain the internal impedance as low as possible.

13 Claims, 3 Drawing Sheets

(51) Int. Cl.

| | |
|---|---|
| *A61N 1/362* | (2006.01) |
| *A61N 1/378* | (2006.01) |
| *H01M 2/06* | (2006.01) |
| *H01M 4/38* | (2006.01) |
| *H01M 10/052* | (2010.01) |
| *H01M 10/058* | (2010.01) |
| *H01M 4/66* | (2006.01) |

(52) U.S. Cl.
CPC ....... *H01M 10/052* (2013.01); *H01M 10/058* (2013.01); *C21D 2211/001* (2013.01)

(56) References Cited

U.S. PATENT DOCUMENTS

| | | | |
|---|---|---|---|
| 3,957,056 A * | 5/1976 | Comben | ............... A61N 1/378 607/36 |
| 4,340,651 A | 7/1982 | Howard et al. | |
| 4,812,376 A | 3/1989 | Rudolph | |
| 5,604,055 A | 2/1997 | Brown et al. | |
| 2009/0104520 A1* | 4/2009 | Marple | ............... H01M 2/022 429/164 |
| 2016/0204391 A1* | 7/2016 | Kraft | ...................... H01M 4/06 429/185 |

OTHER PUBLICATIONS

"Standard Test Methods for Determining Average Grain Size", ASTM International Designation: E112-12, Copyright by ASTM International, Tuesday, Sep. 3, 2013.

* cited by examiner

LITHIUM-IODINE ELECTROCHEMICAL CELLS EXHIBITING LOW DISCHARGE IMPEDANCE

CROSS REFERENCE TO RELATED APPLICATION

This application claims priority to U.S. provisional application Ser. No. 62/541,512, filed on Aug. 4, 2017.

BACKGROUND OF THE INVENTION

1. Field of the Invention

The present invention generally relates to a primary electrochemical cell, and more particularly, to improved discharge performance for an alkali metal-halogen electrochemical cell. The cell is preferably housed inside a stainless steel casing. The improvement is realized by optimizing the grain size of the stainless steel, which affects the impedance at the passivation interface between the cathode and the casing serving as the cathode current collector.

2. Prior Art

Bradycardia is an abnormality of the heart's rhythm in which the heart's "natural pacemaker" is set too slow, resulting in fatigue, dizziness and fainting. This cardiac rhythm disorder can be managed very successfully using an implantable cardiac pacemaker. The pacemaker is implanted in the chest wall and one or more leads run through a large vein into the heart. The electrode leads deliver electrical pulses to the heart muscle and ensure that the heart beats are regular and at an appropriate pace. One of the most important components of the pacemaker is the electrochemical cell that serves as the power source to provide electrical energy for the electronic control system of the pulse generator. Therefore, an electrochemical cell that is designed to power an implantable pulse generator, for example a cardiac pacemaker, is required to provide consistence performance for a long period of time.

Lithium-iodine electrochemical cells are commonly used as the power source for cardiac pacemakers. In a lithium-iodine electrochemical cell, the casing is used as the cathode current collector. Using the cell casing as the cathode current collector is advantageous because it saves space that would otherwise be required for a separate current collector, thus increasing the energy density of the cell. During discharge of the lithium-iodine cell, charge transfer takes place between the iodine-containing cathode material and the casing current collector. Any insulating film formed on the casing impedes this discharge process and increases the internal resistance of the cell.

A typical lithium-iodine cell casing is made by drawing and successive thermal annealing of stainless steel, preferably 304 L stainless steel. Cells built using such casings have been known to exhibit internal impedance variations within the same casing lot as well as in different annealing lots. It is known that a stainless steel casing current collector automatically forms a passivation layer upon exposure to the iodine-containing cathode material, and this passivation layer is important to the internal impedance of a lithium-iodine cell during discharge. Higher internal impedance diminishes the delivered power and consequently the useful life of the pacemaker.

Therefore, there is a need for a stainless steel casing for a lithium-halogen electrochemical cell wherein the annealing process provides the stainless steel with a grain size that when subsequently contacted by an iodine-containing cathode material forms a passivation layer that exhibits a relatively lower impedance during cell discharge. More specifically, the formed passivation layer is of a desired character so that the discharge performance of one lithium-iodine cell to the next is consistent and predictable. A predictable discharge curve is beneficial in letting the physician know when the cell is reaching end-of-life and, consequently, when the cardiac pacemaker needs to be replaced.

SUMMARY OF THE INVENTION

Alkali metal-halogen electrochemical cells, for example lithium-iodine cells are typically constructed having a central lithium anode contacted by an iodine-containing cathode material. The casing for a lithium-iodine cell is preferably of stainless steel and serves as the cathode current collector. According to the present invention, a lithium-iodine electrochemical cell made with a casing of stainless steel having relatively finer grain sizes (ASTM 7 or finer) desirably exhibits lower internal resistance compared to a similar cell made with a stainless steel casing current collector of relatively coarser grain sizes (ASTM 6 or coarser). This behavior is depicted in FIG. 3 where the impedance of a lithium-iodine electrochemical cell comprising a casing of 304 L stainless steel and having a grain size of ASTM 5 (64 µm) was observed to be significantly higher than that of a similar lithium-iodine cell, but where the 304 L stainless steel casing had a grain size in the range of ASTM 7 (32 µm) to ASTM 8.5 (22.4 µm).

Thus, the present invention discloses that the internal impedance during discharge of one lithium-iodine electrochemical cell to the next cell can be consistently maintained in a desirable range by optimizing the grain size of the stainless steel casing material in the manufacturing process. It is believed that the grain size of the stainless steel material for the casing directly affects impedance at the passivation interface between the iodine-containing cathode material and the casing serving as the cathode current collector.

The above aspects of the present invention will become more apparent to those skilled in the art by reference to the following description and to the following drawings.

DETAILED DESCRIPTION OF THE INVENTIONS

In this specification, the term "ASTM grain size" means the ASTM grain size number, G, which is defined as: NAE $=2^{G-1}$ where NAE is the number of grains per square inch at 100×magnification.

It is noted that the lower the ASTM number, the coarser the grain size of a stainless steel material according to the present invention. In that respect, it has been observed that when a stainless steel material serving as the casing current collector for a lithium-iodine electrochemical cell consists of relatively coarser grains (ASTM 6 or coarser), the internal passivation layer is more stable than the passivation layer formed on a stainless steel material consisting of relatively finer grains. However, a relatively more stable passivation layer results in undesirable higher internal resistance. On the other hand, a relatively more unstable internal passivation layer resulting from a stainless steel material having a relatively finer grain size (ASTM 7 or finer) provides a lithium-iodine electrochemical cell having relatively lower internal impedance, which is desirable.

Figure 1:
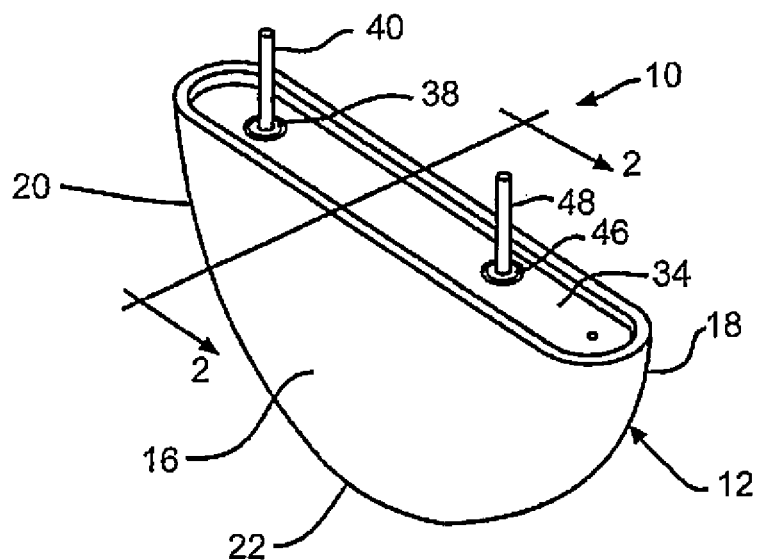
FIG. 1 is a perspective view of an exemplary alkali metal-halogen cell 10 housed in a stainless steel casing 12 according to the present invention.
Figure 2:
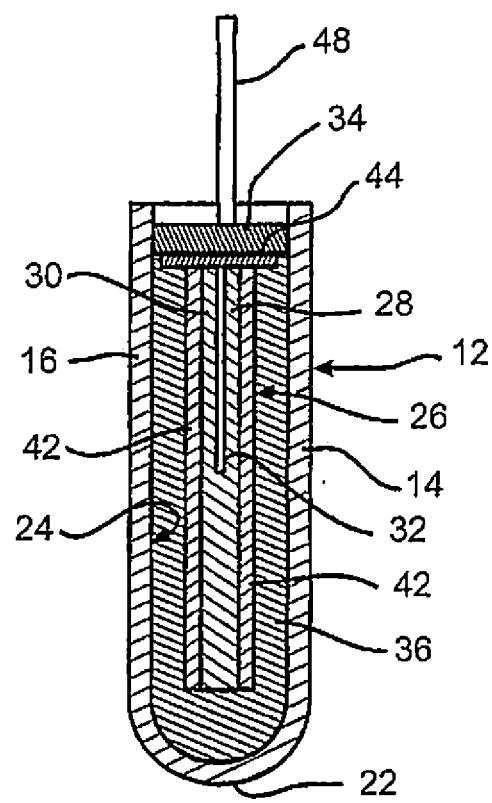
FIG. 2 is an enlarged sectional view taken along line 2-2 in FIG. 1.

Referring now to the drawings, FIGS. 1 and 2 show an exemplary alkali metal-halogen electrochemical cell 10 housed inside of a casing 12 according to the present invention. The casing 12 is of a metal such as stainless steel and includes spaced apart sidewalls 14, 16 joined by curved end walls 18, 20 and a curved bottom wall 22. In accordance with the present invention, prior to assembly of the cell 10 the casing 12 is preferably annealed in a temperature range of from about 1,750° F. to about 1,800° F. for a period of time sufficient to render the stainless steel material having a grain size that ranges from about ASTM 7 (32 μm) to about 8.5 (18 μm). That is to ensure satisfactory electrical performance of the cell during discharge. This phenomenon of grain size dependence on the discharge voltage performance holds for any casing material made from austenitic or precipitation hardened stainless steel with a chromium content of 15 wt % to 20 wt %.

The electrochemical couple housed inside of the casing 12 according to the present invention includes an anode, generally designated 26 and comprising an alkali metal, preferably in the form of a pair of lithium plates 28, 30 pressed together and bonded against an anode current collector 32 of a metal such as nickel or nickel alloy. The anode current collector 32 sandwiched between plates 28, 30 can be of various forms such as a length of wire, a strand or ribbon, or a mesh or screen. Each of the lithium plates 28, 30 in the cell 10 of FIGS. 1 and 2 has generally planar, oppositely directed parallel surfaces. Lithium plate 28 is identical to lithium plate 30 in size and peripheral outline. The two plates are in registry or in alignment when pressed together. The lithium anode may also be deposited on the anode current collector 32 by vacuum deposition, electroplating or other conventional methods.

The open top of casing 12 with the anode 26 and anode current collector 32 positioned therein, as shown in FIG. 2, is closed by a lid 34 provided with a fill opening (not shown). Then, the iodine-containing cathode material 36 is introduced into the casing 12 through the fill opening so that the cathode material is in operative contact with the anode 26 and with the sides 14, 16, bottom 22 and end walls 18, 20 of the conductive metal casing 12, which serves as the cathode current collector.

The anode reaction is:

and the cathode reaction is:

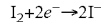

giving an overall reaction of:

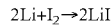

This electrochemical system is especially advantageous in that lithium has a high energy density, as the most electropositive metal with the lowest equivalent weight. The electrolyte formed on discharge of the cell is LiI. This lithium salt has the highest ionic conductivity, much higher than the ionic conductivity of divalent halides.

The cathode material 36 preferably comprises a charge transfer complex of an organic material and iodine, although any other cathode active material may be used that is electronically conductive and contains available iodine for the electrochemical reaction. Charge transfer complexes are a well-known class of materials that have two components, one an electron donor, the other an electron acceptor, and that form weakly bonded complexes exhibiting higher electronic conductivity than either component. Suitable charge transfer complexes for the present invention consist of an organic donor component and iodine, the electron acceptor component, and preferably have a conductivity of greater than about $2.5 \times 10^{-4}$ ohm/cm. The charge transfer complexes are in chemical equilibrium with some small amount of free iodine that is available for electrochemical reaction. These charge transfer complexes have a wide range of electronic conductivities. If the conductivity is low, the current output will be comparatively low because of the high internal ohmic resistance. Cathodes containing intimate mixtures of such low conductivity complexes combined with powdered graphite or inert metal have higher conductivities and can provide electrical discharge performance comparable to cells using high conductivity complexes.

In particular, the cathode material 36 is prepared by heating the organic material mixed with iodine to a temperature greater than the crystallization temperature of iodine, for example about 300° F. The amount of iodine should be greater than about 50 percent by weight of the resulting mixture so that enough iodine is available in the cathode material to provide sufficient conductivity for proper cell operation. The resulting mixture is a viscous, flowable substance, which is preferably introduced into the cell casing 12 by flowing it through the above-mentioned fill opening in lid 34. When filling is completed, a closure element 38, preferably also of stainless steel, is welded to the lid 34 to close the fill opening. A terminal lead 40 is spot welded to the lid. That is done either before or after the closure element 38 is welded to lid 34.

Suitable charge transfer complexes may be prepared using as organic donor components polycyclic aromatic compounds, such as, for example, pyrene, perylene, anthracene, naphthalene, erythrosine, azulene and fluorene; organic polymers, such as, for example, polyethylene, polypropylene, polystyrene, polypyrrole, polyamides and polyvinyls; or heterocyclic compounds, containing nitrogen or sulfur, such as, for example, phenothiazine, phenazine, 10-phenylphenophiozine, thianthrene, 10-methylthiazinc and methalyineblue; and polymerized or polymerizable compounds in which a heterocyclic nitrogen moiety is incorporated as a side chain or substituent, especially vinyl compounds and polymers, such as poly-2-vinyl quinoline, poly-2-vinyl pyridine, poly-4-vinyl pyridine, poly-5-vinyl-2-methyl-pyridine and poly-N-vinyl carbazole. The proportions of iodine as the electron acceptor component to the organic donor component can be varied over a wide range, although a high proportion of uncomplexed iodine in the cathode generally increases internal cell resistance. Other iodine-containing cathodes that are electronically conductive may also be used, such as mixtures of iodine and carbon or graphite.

A lithium-iodide electrolyte 42 is formed in situ through reaction of iodine present in the cathode with the lithium anode. It is equally satisfactory, and in some instances preferable, to form a film of lithium salt electrolyte on the anode surface abutting the cathode prior to cell assembly. That is done most conveniently by exposing the anode surface to dry air or an argon atmosphere containing halogen gas or vapor. It will be recognized that additional lithium-iodide electrolyte is formed by the electrochemical reaction of the cell.

A strip or band of electrical insulating material 44 serves to insulate anode 26 from the metal lid 34 of casing 12 in a completed or assembled cell. An anode lead (not shown) extends from the anode current collector 32, through a glass-to-metal seal serving as an insulator and seal structure 46, to thereby serve as an anode terminal lead 48 extending outwardly from the lid 34. For a more detailed description of such an alkali metal-halogen cell, reference is made to U.S. Pat. No. 4,401,736, issued Aug. 30, 1983 and entitled "Anode Assembly For Lithium Halogen Cell". This patent is assigned to the assignee of the present invention and incorporated herein by reference.

According to the present invention, it has been observed that the stability of the passivation layer that forms on the inner surface of the casing 12 upon exposure to the iodine-containing cathode material is related to the grain size of the stainless steel material of the casing. A passivation layer formed on the inner surface of a stainless steel casing 12 having grains sizes that are coarser than ASTM 6 is believed to be more stable or uniform than a passivation layer formed on stainless steel having finer grain sizes. Therefore, lithium-iodine electrochemical cells made with stainless steel casings 12 having coarser grains (ASTM 6 or coarser) are believed to exhibit higher internal resistance/impedance in comparison to those made with stainless steel casings 12 having finer grains (ASTM 7 or finer).

Figure 3:
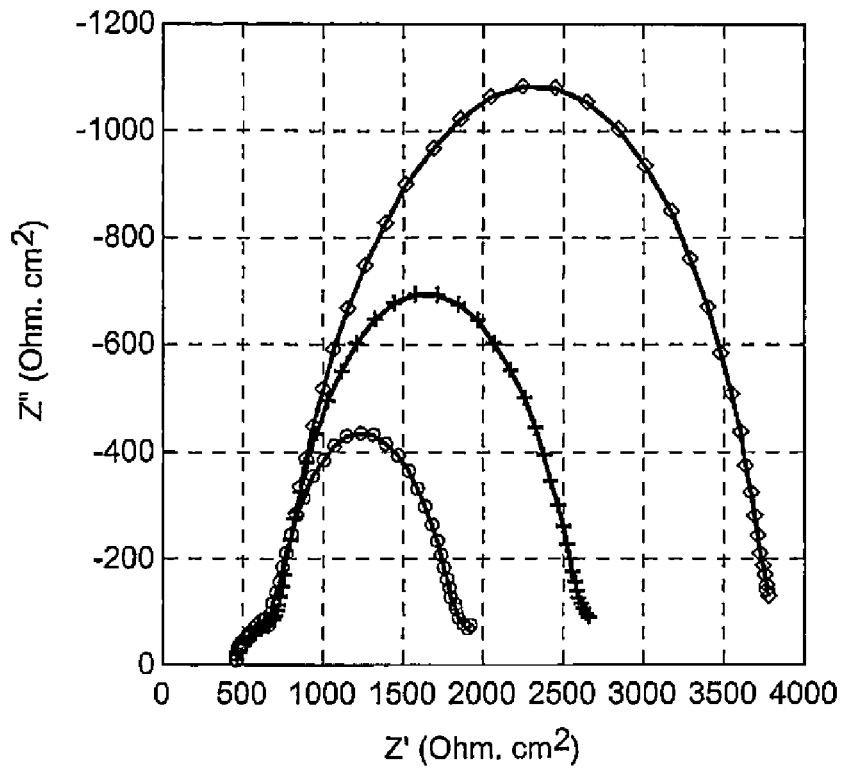
FIG. 3 is a graph of normalized impedance spectra of cells built using casings with different grain sizes.

This is depicted in FIG. 3, which shows the normalized impedance spectra of cells built with casings having different grain sizes. Stainless steel casings with grain sizes of about ASTM 7 to about ASTM 8.5 (about 32 µm to about 18 µm, respectively) are shown to exhibit the lowest maximum internal impedance (<2000 Ohm·cm$^2$) at a frequency of 0.1 Hz. Stainless steel casings with grain sizes of about ASTM 6 to about ASTM 6.5 are shown to exhibit a maximum internal impedance between about 2,500 Ohm·cm$^2$ and 3,000 Ohm·cm$^2$, respectively, at a frequency of 0.1 Hz. Stainless steel casings with grain sizes below about ASTM 5 are shown to exhibit a maximum internal resistance above 3,000 Ohm·cm$^2$ at a frequency of 0.1 Hz.

In accordance with the present invention, the grain size of stainless steel used to construct a casing for a lithium-iodine electrochemical cell is about ASTM 6 or finer, preferably, about ASTM 7 or finer, and more preferably from about ASTM 7.5 to about ASTM 8.5, to thereby lower the impedance of the interface between the cathode and the passivation layer that forms on the inner surface of the casing 12 serving as the cathode current collector upon contact with the iodine-containing cathode material. As used herein and in the claims, the term "grain size" or "grain number" are meant to refer to the average grain size.

Figure 4:
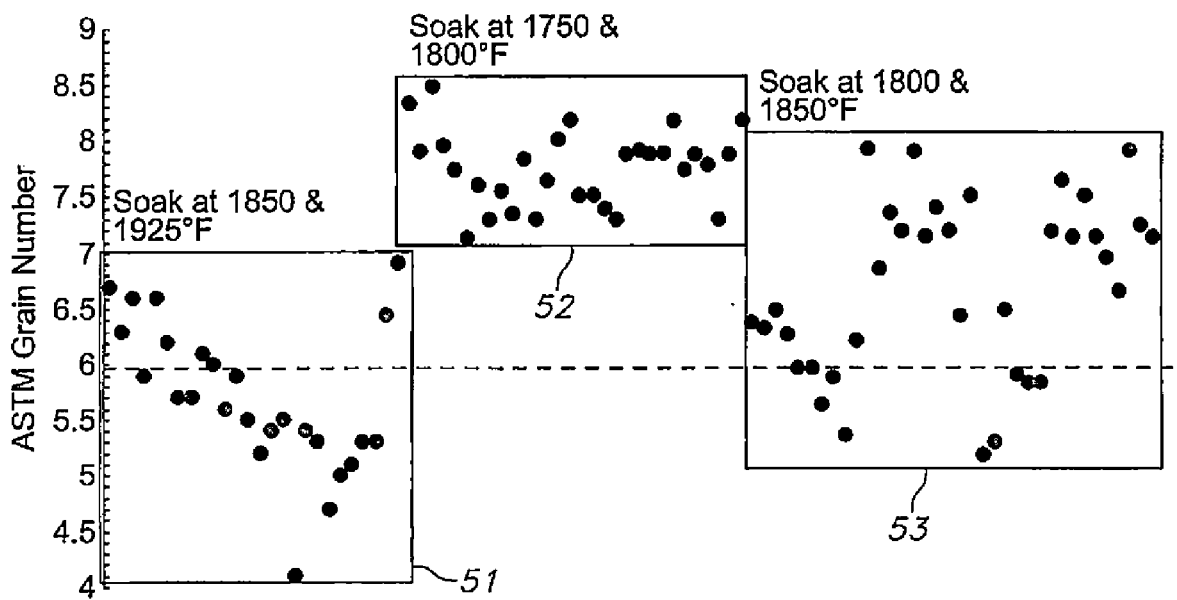
FIG. 4 is a graph of ASTM grain number distribution for 304 L stainless steel cell casings carried out in annealing cycle temperature ranges from about 1,750° F. to about 1,925° F.

Accordingly, thermal annealing parameters related to the casing manufacturing process govern the grain size of the final microstructure. Experiments were conducted to lower the final annealing soak temperature, and their results are shown in FIG. 4. The iron-carbon binary phase diagram (not shown) shows that the annealing temperature for stainless steel cannot be below about 1,670° F. If it is, then instead of forming a single-phase austenite, the microstructure will precipitate a secondary alpha iron phase. Moreover, the phenomenon of grain size dependence on the annealing parameters holds for any casing material made from austenitic or precipitation hardened stainless steel with a chromium content of 15 wt % to 20 wt %.

In order to achieve the desired dimensions for a casing, cold working of stainless steel may need to involve multiple steps of successive deep drawing and annealing. In each cycle, the 304 L stainless steel is first drawn, then annealed at a temperature of about 1,750° F. for a soak time of about 30 minutes, drawn again, then annealed at a temperature of about 1,800° for a soak time of about 10 minutes.

Each dot in FIG. 4 represents the post annealed grain size for a sample 304 L stainless steel cell casing carried out in the annealing cycle temperature range indicated for the specific box (of boxes 51, 52, and 53) in which it is located. The casings processed in the annealing temperature range of about 1850° F. to about 1925° F. (box 51) resulted in ASTM grain sizes of about 4 (90 µm) to about ASTM 7 (32 µm). As previously discussed and with particular applicability to the coarser grain sizes below ASTM 7 down to ASTM 4, a coarser stainless steel microstructure adversely affects the internal impedance of a lithium-iodine cell. Further, stainless steel casings processed in the annealing temperature range of about 1,800° F. to about 1,850° F. (box 53) resulted in ASTM grain size as fine as about 8, but undesirably as coarse as about ASTM 5. However, stainless steel casings processed in an annealing temperature range of about 1,750° F. to about 1,800° F. (box 52) were tightly distributed in a desirable range of ASTM grain sizes of about 7 to about 8.5. In that light, lithium-iodine cells built using stainless steel casings subjected to an about 1,750° F. to about 1,800° F. annealing cycle exhibited consistent performance in terms of burn-in and discharge voltage data.

Figure 5:
FIG. 5 is an etched optical micrograph of 304 L stainless steel cell casings in accordance with the prior art.
Figure 6:
FIG. 6 is an etched optical micrograph of 304 L stainless steel cell casings in accordance with the present invention.

FIG. 5 is an etched optical micrograph of 304 L stainless steel cell casings in accordance with the prior art. In contrast, FIG. 6 is an etched optical micrograph of a 304 L stainless steel cell casing with finer grains (ASTM grain 8) annealed in the temperature range of about 1,750° F. to about 1,800° F. in accordance with the present invention.

Thus, it is preferred that the stainless steel grain size for the casing of a lithium-iodine electrochemical cell be about ASTM 7 or finer to maintain an internal impedance at or below 3,000 Ohm·cm$^2$ at a frequency of 0.1 Hz. More preferably, the stainless steel grain size is about ASTM 7 to about ASTM 8.5. Such fine grain sizes desirably lower the impedance during cell discharge.

While 304 L stainless steel was used in all of the experiments discussed herein, it is believed that the parameters of the present invention can be reasonably extended to other stainless steels, which have similar features, especially other good corrosion resistance grades of stainless steel, namely grades 300 stainless steel, 304 stainless steel, and 316 stainless steel, to thereby provide similar grain sizes that similarly lower impedance during discharge. Moreover, the phenomenon of grain size dependence on the discharge voltage performance of a lithium-iodine electrochemical cell holds for any casing material made out of austenitic or precipitation hardened stainless steel with a chromium content of 15 to 20 wt.

It should thus be understood that, while the present invention has been described in detail herein, the invention can be embodied otherwise without departing from the principles thereof, and such other embodiments are meant to come within the scope of the present invention as defined by the appended claims.

What is claimed is:

1. An electrochemical cell, comprising:
   a) an open-ended casing closed by a lid, wherein the casing is 304L stainless-steel having a chromium content of from 15 wt % to 20 wt %, and wherein the casing is characterized as having been annealed at a temperature ranging from 1,750° F. to 1,800° F. so that the 304 L stainless-steel has a grain size that ranges from about ASTM 7 to about ASTM 8.5;

b) a lithium-containing anode disposed inside the casing; and c) a cathode comprising a charge transfer complex of an organic donor component and iodine as an electron acceptor component disposed inside the casing, wherein the charge transfer complex is in operative contact with the lithium-containing anode and the casing so that the open-ended casing closed by the lid serves as a cathode current collector.

2. The electrochemical cell of claim 1, having an impedance of about 3,000 Ohm.cm$^2$, or less, at a frequency of 0.1 Hz.

3. The electrochemical cell of claim 1, wherein iodine as the electron acceptor component of the charge transfer complex has a conductivity of greater than about $2.5 \times 10^{-4}$ ohm/cm.

4. The electrochemical cell of claim 1, wherein the organic donor component of the charge transfer complex is selected from the group of pyrene, perylene, anthracene, naphthalene, erythrosine, azulene, fluorene, polyethylene, polypropylene, polystyrene, polypyrrole, polyamides and polyvinyls, phenothiazine, phenazine, 10-phenylphenophiozine, thianthrene, 10-methylthiazinc, methalyineblue, poly-2-vinyl quinoline, poly-2-vinyl pyridine, poly-4-vinyl pyridine, poly-5-vinyl-2-methyl-pyridine, and poly-N-vinyl carbazole.

5. The electrochemical cell of claim 1, wherein an anode conductor is operatively connected to the lithium-containing anode, the anode conductor being electrically isolated from the casing by a glass-to-metal seal.

6. The electrochemical cell of claim 1 being configured to power a cardiac pacemaker.

7. An electrochemical cell, comprising:
a) a casing comprised of 304L stainless-steel having a chromium content of from 15 wt % to 20 wt %, wherein the casing is characterized as having been annealed at a temperature ranging from 1,750° F. to 1,800° F. so that the 304 L stainless-steel has a grain size that ranges from about ASTM 7 to about ASTM 8.5;

b) a lithium-containing anode disposed inside the casing; and c) a cathode comprising a charge transfer complex of an organic donor component and iodine as an electron acceptor component disposed inside the casing, wherein the charge transfer complex is in operative contact with the lithium-containing anode and the casing so that the casing serves as a cathode current collector.

8. The electrochemical cell of claim 7, wherein the organic donor component of the charge transfer complex is selected from the group of pyrene, perylene, anthracene, naphthalene, erythrosine, azulene, fluorene, polyethylene, polypropylene, polystyrene, polypyrrole, polyamides and polyvinyls, phenothiazine, phenazine, 10-phenylphenophiozine, thianthrene, 10-methylthiazinc, methalyineblue, poly-2-vinyl quinoline, poly-2-vinyl pyridine, poly-4-vinyl pyridine, poly-5-vinyl-2-methyl-pyridine, and poly-N-vinyl carbazole.

9. The electrochemical cell of claim 7, having an impedance of about 3,000 Ohm.cm$^2$, or less, at a frequency of 0.1 Hz.

10. A method for making a low internal impedance alkali metal-iodine electrochemical cell, comprising the steps of:
a) providing an open-ended casing of 304L, stainless-steel having a chromium content of from 15 wt % to 20 wt %;

b) annealing the casing at a temperature ranging from 1,750° F. to 1,800° F. so that the 304 L stainless-steel has a grain size that ranges from about ASTM 7 to about ASTM 8.5 or finer;

c) positioning a lithium-containing anode inside the open-ended casing;

d) closing the open end of the casing with a lid;

e) filling a charge transfer complex of an organic donor component and iodine as an electron acceptor component into the casing through a fill opening in the lid so that the charge transfer complex contacts the lithium-containing anode and the casing, wherein a passivation layer forms on an inner surface of the 304 L stainless-steel casing as a result of contact with the charge transfer complex; and f) closing the fill opening.

11. The method of claim 10, including providing iodine as the electron acceptor component of the charge transfer complex having a conductivity of greater than about $2.5 \times 10^{-4}$ ohm/cm.

12. An open-ended casing for an electrochemical cell, the casing comprising:
a) 304 L stainless-steel having a chromium content of from 15 wt % to 20 wt %, b) wherein the casing is characterized as having been annealed at a temperature ranging from 1,750° F. to 1,800° F. so that the 304 L stainless steel has a grain size that ranges from about ASTM 7 to about ASTM 8.5.

13. The method of claim 10, including selecting the organic donor component of the charge transfer complex from the group of pyrene, perylene, anthracene, naphthalene, erythrosine, azulene, fluorene, polyethylene, polypropylene, polystyrene, polypyrrole, polyamides and polyvinyls, phenothiazine, phenazine, 10-phenylphenophiozine, thianthrene, 10-methylthiazinc, methalyineblue, poly-2-vinyl quinoline, poly-2-vinyl pyridine, poly-4-vinyl pyridine, poly-5-vinyl-2-methyl-pyridine, and poly-N-vinyl carbazole.

* * * * *

UNITED STATES PATENT AND TRADEMARK OFFICE
CERTIFICATE OF CORRECTION

| | |
|---|---|
| PATENT NO. | : 10,790,482 B2 |
| APPLICATION NO. | : 16/048984 |
| DATED | : September 29, 2020 |
| INVENTOR(S) | : Lasantha Viyannalage et al. |

It is certified that error appears in the above-identified patent and that said Letters Patent is hereby corrected as shown below:

In the Specification

Column 4, Line 60 delete "uncomplexed" and insert --un-complexed--

In the Claims

Column 8, Line 14 (Claim 10) delete "304L," and insert --304L--

Column 8, Line 20 (Claim 10) delete "or finer"

Column 8, Line 40 (Claim 12) correct the claim formatting error, so that "b)" and its respective text aligns correspondingly to the line indent of a) of Claim 12

Signed and Sealed this
Ninth Day of May, 2023

Katherine Kelly Vidal
*Director of the United States Patent and Trademark Office*